United States Patent
Karavitis et al.

(10) Patent No.: US 12,357,843 B2
(45) Date of Patent: Jul. 15, 2025

(54) METHODS OF SKIN TREATMENT WITH LASER LIGHT

(71) Applicant: CUTERA, INC., Brisbane, CA (US)

(72) Inventors: Michael A. Karavitis, San Pedro, CA (US); Amogh Kothare, Fremont, CA (US)

(73) Assignee: Cutera, Inc., Brisbane, CA (US)

( * ) Notice: Subject to any disclaimer, the term of this patent is extended or adjusted under 35 U.S.C. 154(b) by 0 days.

(21) Appl. No.: 17/972,557

(22) Filed: Oct. 24, 2022

(65) Prior Publication Data

US 2023/0302295 A1 Sep. 28, 2023

Related U.S. Application Data

(60) Provisional application No. 63/324,017, filed on Mar. 25, 2022.

(51) Int. Cl.
| | | |
|---|---|---|
| A61N 5/067 | (2006.01) | |
| A61B 18/00 | (2006.01) | |
| A61B 18/20 | (2006.01) | |
| A61N 5/00 | (2006.01) | |
| A61N 5/06 | (2006.01) | |

(52) U.S. Cl.
CPC ........... *A61N 5/067* (2021.08); *A61N 5/0616* (2013.01); *A61N 2005/007* (2013.01); *A61N 2005/0659* (2013.01)

(58) Field of Classification Search
CPC ...... A61B 18/20–18/28; A61N 5/06–2005/073
USPC .................... 606/2–19; 607/88–94
See application file for complete search history.

(56) References Cited

U.S. PATENT DOCUMENTS

| | | | |
|---|---|---|---|
| 6,419,642 B1 | 7/2002 | Marchitto et al. | |
| 6,425,873 B1 | 7/2002 | Marchitto et al. | |
| 6,524,242 B2 * | 2/2003 | Subramanyan | ........ A61B 5/441 600/306 |
| 6,866,659 B2 | 3/2005 | Nemati | |
| 7,118,868 B2 | 10/2006 | Berlin | |
| 7,259,109 B2 | 8/2007 | Meagley | |
| 8,323,273 B2 | 12/2012 | Rylander et al. | |
| 9,105,458 B2 | 8/2015 | Trimpin et al. | |
| 9,168,388 B2 | 10/2015 | Rylander et al. | |

(Continued)

FOREIGN PATENT DOCUMENTS

JP 2008531133 * 8/2008

OTHER PUBLICATIONS

Vargas, Gracie et al., "Use of an Agent to Reduce Scattering in Skin," in Lasers in Surgery and Medicine.

(Continued)

*Primary Examiner* — Jonathan T Kuo
*Assistant Examiner* — Vynn V Huh
(74) *Attorney, Agent, or Firm* — McCarter & English, LLP (57) ABSTRACT

Dermatological systems and methods for reducing pain associated with treating of skin with high-fluence therapeutic laser light including applying a first agent to solubilize oils, removing the first agent and oil to reduce the level of oil in the skin by at least 85%, rehydrating the skin after the oil removal, applying a contact cooling element including a cooling window to the area within five minutes of rehydrating the skin, cooling the skin from a first to a second temperature, and applying at least one high-fluence therapeutic laser pulse to the skin.

20 Claims, 7 Drawing Sheets

Fig. 6

(56) References Cited

U.S. PATENT DOCUMENTS

| | | |
|---|---|---|
| 9,364,287 B2 | 6/2016 | DeBenedictis et al. |
| 9,615,750 B2 | 4/2017 | Liopo et al. |
| 10,369,170 B1 | 8/2019 | Buck |
| 2001/0050083 A1 | 12/2001 | Marchitto et al. |
| 2004/0152080 A1 | 8/2004 | Berlin |
| 2005/0107399 A1 | 5/2005 | Boman et al. |
| 2005/0154382 A1* | 7/2005 | Altshuler ............ A61B 18/203 606/9 |
| 2006/0003948 A1 | 1/2006 | Krasutsky et al. |
| 2006/0121489 A1 | 6/2006 | Gorenstein et al. |
| 2006/0267156 A1 | 11/2006 | Meagley |
| 2007/0207284 A1 | 9/2007 | McClintic |
| 2007/0299431 A1 | 12/2007 | Jakubowski et al. |
| 2008/0038376 A1 | 2/2008 | Giles |
| 2008/0097557 A1 | 4/2008 | Eggers et al. |
| 2008/0097559 A1 | 4/2008 | Eggers et al. |
| 2008/0215039 A1 | 9/2008 | Slatkine et al. |
| 2009/0053290 A1 | 2/2009 | Sand et al. |
| 2010/0261176 A1 | 10/2010 | Mitragotri et al. |
| 2011/0135571 A1 | 6/2011 | Lin et al. |
| 2011/0190745 A1 | 8/2011 | Uebelhoer et al. |
| 2012/0059307 A1 | 3/2012 | Harris et al. |
| 2013/0041308 A1 | 2/2013 | Hennings et al. |
| 2013/0306856 A1 | 11/2013 | Trimpin et al. |
| 2015/0196639 A1* | 7/2015 | Lando ..................... A61N 7/00 604/20 |
| 2016/0018361 A1 | 1/2016 | Trimpin et al. |
| 2016/0030726 A1 | 2/2016 | Hwang et al. |
| 2017/0165194 A1 | 6/2017 | Meng et al. |
| 2018/0236260 A1* | 8/2018 | Tagliaferri ........... A61B 18/203 |
| 2019/0227032 A1 | 6/2019 | Trimpin et al. |
| 2020/0190158 A1 | 6/2020 | Eveleth et al. |
| 2020/0230081 A1 | 7/2020 | Pathak |
| 2020/0258729 A1 | 8/2020 | Karancsi et al. |
| 2020/0343084 A1 | 10/2020 | Trimpin et al. |

OTHER PUBLICATIONS

Vargas, Gracie et al., "Use of Hyperosmotic Chemical Agent to Improve the Laser Treatment of Cutaneous Vascular Lesions," in Journal of Biomedical Optics, vol. 13, No. 2, 021114-1 to 02114-8, (Mar./Apr. 2008).

Mcnicols, Roger J. et al., "Temporary Dermal Scatter Reduction: Quantitative Assessment and Implications for Improved Laser Tattoo Removal," in Lasers in Surgery and Medicine, vol. 36, 289-296 (2005).

Khan, Misbah H. et al., "Can Topically Applied Optical Clearing Agents Increase the Epidermal Damage Threshold and Enhance Therapeutic Safety," in Lasers in Surgery and Medicine, vol. 35 No. 2, 93-95 (2004).

Hanslick, Jennifer L. et al., "Dimethyl Sulfoxide (DMSO) Produces Widespread Apoptosis in the Developing Central Nervous System," in Neurobiology of Disease, vol. 34, 1-10 (2009).

Bui, Albert K. et al., "Revisiting Optical Clearing with Dimethyl Sulfoxide (DMSO)," in Lasers in Surgery and Medicine vol. 41, 142-148 (2009).

\* cited by examiner

| Pt. ID | Sebumeter Reading | | | Ratio POST /PRE Wash | Δ POST /PRE Wash | Ratio Acetone /PRE Wash | Δ Acetone /PRE Wash | Ratio Acetone /POST Wash | Δ Acetone /POST Wash |
|---|---|---|---|---|---|---|---|---|---|
| | Before Face Wash | After Face Wash | After Acetone Wipe | | | | | | |
| 1-R | 78 | 15 | 1 | 19% | 81% | 1% | 99% | 7% | 93% |
| 1-L | 54 | 10 | 1 | 19% | 81% | 2% | 98% | 10% | 90% |
| 2-R | 50 | 8 | 0 | 16% | 84% | 0% | 100% | 0% | 100% |
| 2-L | 38 | 7 | 0 | 18% | 82% | 0% | 100% | 0% | 100% |
| 3-R | 71 | 20 | 0 | 28% | 72% | 0% | 100% | 0% | 100% |
| 3-L | 94 | 15 | 1 | 16% | 84% | 1% | 99% | 7% | 93% |
| 4-R | 58 | 13 | 1 | 22% | 78% | 2% | 98% | 8% | 92% |
| 4-L | 73 | 15 | 2 | 21% | 79% | 3% | 97% | 13% | 87% |
| 5-R | 107 | 14 | 0 | 13% | 87% | 0% | 100% | 0% | 100% |
| 5-L | 102 | 13 | 0 | 13% | 87% | 0% | 100% | 0% | 100% |

Fig. 4

| Pt. ID | Fluence (J/cm2) | Discomfort - No DMSO | Discomfort - DMSO | Δ |
|---|---|---|---|---|
| 1 | 27.5 | 4 | 2 | 50% |
| 2 | 25 | 5 | 4 | 20% |
| 3 | 27.5 | 4 | 3 | 25% |

METHODS OF SKIN TREATMENT WITH LASER LIGHT

CROSS-REFERENCE TO RELATED APPLICATIONS

This invention claims the benefit of priority to U.S. Provisional Application Ser. No. 63/324,017 filed Mar. 25, 2022, entitled "Image Guided Laser Therapy," which is hereby incorporated by reference herein in its entirety.

BACKGROUND OF THE DISCLOSURE

This disclosure relates generally to methods of treatment for medical devices and more particularly, to methods, apparatus, and systems for reducing a level of perceived pain associated with the delivery of high-fluence laser light to skin to treat a medical condition.

DESCRIPTION OF THE RELATED ART

Laser systems are used to treat a variety of dermatological conditions. Such systems may employ laser light having a high fluence, which as used herein refers to fluences of 5 J/cm2 and higher. Laser systems have been used for treatment of abnormal skin pigmentation, body sculpting (e.g., removal of subcutaneous adipose tissue), hair removal, treatment of vascular skin conditions (e.g., spider veins), reduction of wrinkles and fine lines, and dyschromia, among other conditions. Abnormal pigmentation conditions may include tattoos and benign pigmented lesions associated with high local concentrations of melanin in the skin, such as freckles, age spots, birthmarks, lentigines, and nevi, among other pigmentation conditions. Both pulsed and continuous-wave (CW) laser systems have been used to treat pigmentation conditions, although pulsed lasers are more frequently used. In many instances, the target for the laser may lie below the epidermis and in the dermis. In general, because of scattering effects and the absorbance of the laser light by overlying tissues (typically resulting in heating the tissue), deeper targets are associated with higher laser fluences to ensure that sufficient energy penetrates superficial tissues to reach the target. Frequency such high-fluence light can result in discomfort or pain to the patient.

In many instances, the absorption coefficient of the target (e.g., tattoo ink particles for tattoos, melanin or other skin pigments, or sebum) of the laser light may be similar to other chromophores such as water or blood that are also present in the skin (see discussion of FIGS. 3A-3B hereinafter). There is a need for improved treatments to reduce pain levels associated with laser treatments utilizing high-fluence laser light.

SUMMARY OF THE DISCLOSURE

In one embodiment, the present disclosure comprises a method of reducing a level of pain perceived by a patient in response to a pain-inducing treatment of a target skin area with high-fluence therapeutic laser light, the target skin area comprising an epidermis layer and a dermis layer, the method comprising: a) applying to a stratum corneum of a first skin area of a patient a first agent adapted to solubilize oils secreted by the skin, the stratum corneum having a first level of skin oil associated therewith; b) removing at least a portion of the first agent and skin oil to reduce the first level of skin oil by at least 85%; c) after said removing, applying a rehydrating solution to the first skin area to reduce entrapped air within the stratum corneum of the first skin area; d) applying a contact cooling element comprising a cooling window to the first skin area within a time interval of 5 minutes after applying the rehydrating solution to the first skin area, wherein the contact cooling window comprises a material that is transmissive to high-fluence therapeutic laser pulse having a first wavelength, and cooling the first skin area from a first temperature to a second temperature; and e) after cooling the first skin are to the second temperature, applying at least one high-fluence therapeutic laser pulse having the first wavelength to at least one target skin area within the first skin area.

In another embodiment, the present disclosure comprises a method of treating the skin of a patient to reduce a level of pain associated with treating a target skin area with high-fluence therapeutic laser light, the target skin area comprising an epidermis layer and a dermis layer, the method comprising: a) applying to an epidermis of a first skin area of the patient an oil-removing agent, the epidermis of the first skin area having a first level of skin oil associated therewith; b) removing at least a portion of the oil-removing agent and skin oil sufficient to reduce the first level of skin oil in the epidermis of the first skin area by at least 85%; c) after said removing, applying a rehydrating solution to the epidermis of the first skin area to reduce entrapped air within the epidermis of the first skin area; d) applying a contact cooling element comprising a cooling window to the first skin area within a time interval of 5 minutes after applying the rehydrating solution to the epidermis of the first skin area, wherein the contact cooling window comprises a material that is transmissive to high-fluence therapeutic laser pulse having a first wavelength, and cooling the first skin area from a first temperature to a second temperature; and e) after cooling the first skin are to the second temperature, applying at least one high-fluence therapeutic laser pulse having the first wavelength to at least one target skin area within the first skin area.

In another embodiment, the present disclosure comprises a method of treating the skin of a patient to reduce a level of pain associated with treating a target skin area with high-fluence therapeutic laser light, the target skin area comprising an epidermis layer and a dermis layer, the method comprising: a) applying to a stratum corneum of a first skin area of a patient an aqueous agent to clean the skin, the stratum corneum having a first level of skin oil associated therewith; b) removing at least a portion of the first agent and oil to reduce the first level of skin to a second level of skin oil that is that is from 0-50% less than the first level of skin oil; c) after said removing of the first agent and oil, applying to the stratum corneum of the first skin area a second agent adapted to solubilize oils secreted by the skin; d) removing at least a portion of the second agent and skin oil to reduce the level of skin oil to a third level of skin oil that is at least 85% less than the first level of skin oil; e) after said removing of the second agent and oil, applying a rehydrating solution to the first skin area to reduce entrapped air within the stratum corneum of the first skin area; f) applying a contact cooling element comprising a cooling window to the first skin area within a time interval of 5 minutes after applying the rehydrating solution to the first skin area, wherein the contact cooling window comprises a material that is transmissive to high-fluence therapeutic laser pulse having a first wavelength, and cooling the first skin area from a first temperature to a second temperature; and g) after cooling the first skin are to the second temperature, applying at least one high-fluence therapeutic laser pulse having the first wavelength through the cooling window to at least one target skin area within the first skin area.

In another embodiment, the present disclosure comprises a method of reducing a level of pain perceived by a patient in response to a pain-inducing treatment of a target skin area with high-fluence therapeutic laser light, the target skin area comprising an epidermis layer and a dermis layer, the method comprising: a) applying an optical clarifying agent to at least a target skin area within a first skin area of a human patient; b) waiting for a first time interval ranging from 30 seconds to 60 minutes after applying the optical clarifying agent to reduce optical scattering in at least the target skin area of the first skin area; c) applying to a stratum corneum of the first skin area a first agent adapted to solubilize oils secreted by the skin, the stratum corneum having a first level of oil associated therewith; d) removing at least a portion of the solvent and oil to reduce the first level of oil by at least 85%; e) applying a rehydrating solution to the stratum corneum of the first skin area after the removing step to reduce entrapped air within the stratum corneum; f) applying a contact cooling element comprising a cooling window to the first skin area after the first time interval has elapsed and within 5 minutes after applying the rehydrating solution to the stratum corneum, wherein the contact cooling window comprises a material that is transmissive to high-fluence therapeutic laser pulse having a first wavelength; and g) applying at least one high-fluence therapeutic laser pulse having the first wavelength to at least the target portion of the first skin area to treat the target skin area of the patient.

In another embodiment, the present disclosure comprises a method of treating the skin of a patient to reduce a level of pain associated with treating a target skin area with high-fluence therapeutic laser light, the target skin area comprising an epidermis layer and a dermis layer, the method comprising: a) applying a solution comprising dimethyl sulfoxide (DMSO) at a concentration of 0.1-80.0 percent DMSO to an epidermis of a first skin area of a patient; b) waiting for a first time interval of from 1-50 minutes to allow the solution to penetrate into the first skin area; c) applying a contact cooling element comprising a cooling window to at least a first portion of the first skin area after the first time interval has elapsed, wherein the contact cooling window comprises a material that is transmissive to high-fluence therapeutic laser light having a first wavelength; d) cooling the at least a first portion of the first skin area from a first temperature to a second temperature; and e) after said cooling, applying therapeutic laser light having the first wavelength and a fluence of 5-40 J/cm2 to at least one target skin area within the at least a first portion of the first skin area, whereby the solution penetrates into the at least one target skin area so as to reduce the level of pain experienced by the patient associated with the application of the high-fluence therapeutic laser light.

BRIEF DESCRIPTION OF THE DRAWINGS

The disclosure may be understood by reference to the following description taken in conjunction with the accompanying drawings in which.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure.

DETAILED DESCRIPTION OF SPECIFIC EMBODIMENTS

Illustrative embodiments of the disclosure are described herein. For clarity, not all features of an actual implementation are provided in detail. In any actual embodiment, numerous implementation-specific decisions must be made to achieve the design-specific goals. Such a development effort, while possibly complex and time-consuming, would nevertheless be a routine task for persons of skill in the art given this disclosure.

This application does not intend to distinguish between components that differ in name but not function. "Including" and "includes" are used in an open-ended fashion, and should be interpreted to mean "including, but not limited to." "Couple" or "couples" are intended to mean either a direct or an indirect electrical connection. "Or" is used in the inclusive sense (i.e., "and/or") unless a specific use to the contrary is explicitly stated.

Figure 1:
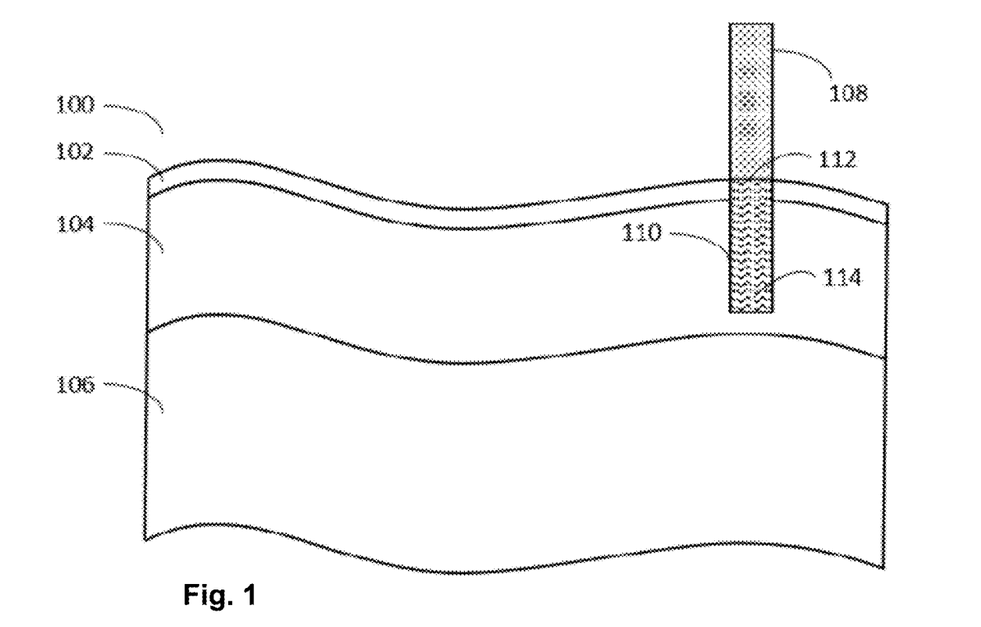
FIG. 1 is a cross-sectional illustration of skin tissue depicting the epidermis, dermis, and hypodermis, with a laser pulse applied to a portion thereof.

FIG. 1 is a side view illustrating a cross-sectional view of a portion 100 of the skin of a patient, including the outermost epidermis 102, the middle layer or dermis 104, and the bottom layer or hypodermis 106. The epidermis 102 has a thickness of about 80-100 μm, which may vary from patient to patient, and even for a single patient depending upon age, health status, and other factors. It includes up to five sub-layers (not shown) and acts as an outer barrier. In particular, the stratum corneum is the outermost layer of the epidermis.

The dermis 104 has a thickness of about 1-5 mm (1000-5000 μm). It contains the blood vessels, nerves, hair follicles, collagen and sweat glands within the skin. Because skin conditions frequently involve structures in the dermis, many laser systems must include sufficient energy to penetrate into the dermis to reach and treat structures therein. Careful selection of a number of parameters must be made in the design and construction of laser systems for treatment of a variety of skin conditions to achieve a desired level of damage to a target structure while minimizing or avoiding damage to non-targeted (e.g., overlying) structures. For example, incorrect selection of the laser wavelength, pulse width, energy per pulse, the use (or nonuse) of a seed laser, or the pump energy of the laser source or amplifier may result in undesired damage as well as poor performance in treating a dermal structure of interest. Numerous other system choices, such as the use or non-use of an articulating arm for delivery of the laser light to a handpiece for application to the patient's skin, may also affect overall system performance.

The lowest layer of the skin is the hypodermis 106, which includes adipose tissue and collagen. The hypodermis 106 helps control body temperature by insulating the structures of the body below the skin. In addition, the hypodermis protects the inner body tissues from damage by absorbing shock and impacts from outside the body. Because the hypodermis contains fat, its thickness varies widely from person to person based on diet, genetic makeup, and other factors.

FIG. 1 depicts a laser beam 108 applied to a target skin area 110 of the skin 100. The target skin area 110 comprises a surface skin area 112, as well as underlying skin tissue 114 that absorbs at least a portion of the energy of the laser beam 108.

Figure 2:
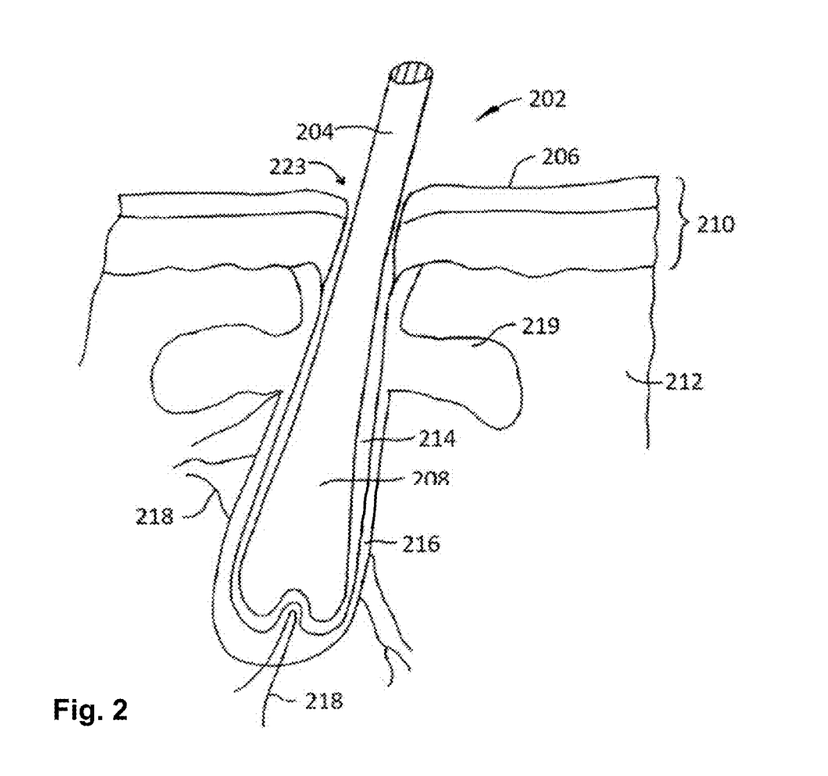
FIG. 2 is a cross-sectional illustration of skin tissue depicting a hair follicle and a sebaceous gland.

FIG. 2 is a side view of the skin of a patient illustrating in simplified form, a hair 202 including a hair shaft 204 extending beyond the exterior skin surface 206. Hair shaft 204 includes a root 208 located below epidermis 210 in the dermis 212. The base, or papilla, of root 208 is located about 4 mm below exterior skin surface 206. Root 208 is housed within hair follicle 214 and is surrounded by tissues including connective tissue sheath 216 and blood vessels 218. Follicle 214 includes a sebaceous gland 219 below an opening 223. Sebaceous glands such as gland 219 are typically located at depths ranging from about 0.3 mm (300 µm) to about 2.0 mm (2000 µm) below exterior skin surface 206, but their depth varies depending upon body location.

Epidermis 210 includes melanin (not shown), a dark pigment found in tissues of the hair, skin and eyes. Melanin, the primary determinant of skin color, is located within globular structures known as melanosomes, which are produced by skin cells called melanocytes. Darker skin has more melanosomes (and thus more melanin) per unit skin area compared to lighter skin. Laser systems targeting deeper structures such as sebaceous gland 219 in the dermis may present a higher risk of patient discomfort where wavelengths having a relatively high absorption coefficient in melanin are used. Without being bound by theory, when laser light at wavelengths readily absorbed by melanin is applied to dark skin (or dark tattoos having ink particles that absorb laser light at similar wavelengths to melanin), the energy absorbed by the melanin (or tattoo ink particles) attenuates part of the laser energy that otherwise would reach deeper structures absent the melanin or ink particles, heating the skin of the epidermis and/or upper dermis to a greater degree than lighter/un-tattooed skin. Additional energy—either by providing higher fluences, higher energy per pulse, or longer treatment times—must be applied to reach deeper structures to heat them to a target treatment temperature. However, higher pulse fluences and pulse energy may compound the problem, since the additional energy delivered in a shorter time period will cause the skin temperature to rise even faster than using lower fluences or energies. In addition, longer treatment times can only deliver more energy to the target if the energy is delivered within the TRT of the target tissue—otherwise, the additional energy largely leaks from the target tissue into adjacent non-target tissue.

Accordingly, in one aspect, the present invention provides laser treatment systems to minimize discomfort by adjusting one or more parameters based on the skin type of the patient. In one embodiment, the invention provides systems and methods for determining a skin type of a patient and automatically adjusting one or more treatment parameters based on the skin type of the patient. This may involve, for patients having darker skin types, one or more of: providing additional cooling of the patient's skin prior to applying a laser therapy to the patient's skin; lowering a first skin temperature at which a therapy pulse is initiated and applied to the patient's skin; lowering a fluence of a laser therapy; lowering a peak power of the laser pulses of a laser therapy; providing a longer pulse width of a pulsed laser therapy; and providing a larger beam diameter for a pulsed laser therapy.

Successful treatment of acne involves damaging sebocytes and/or sebaceous glands. This involves heating sebum, which produced by and located within the sebaceous glands, to damage the gland. Accordingly, it is desirable to select a wavelength of light that is highly absorbed by sebum, preferably more so than competing skin chromophores (e.g., water), to limit the damage to non-targeted tissue and concentrate the laser energy delivered into the targeted sebaceous gland to the exclusion of non-targeted tissues and structures. In addition, because sebaceous glands are relatively deep structures located in the dermis at depths of 300-2000 µm (0.3-2.0 mm), it is desirable to select a wavelength of light capable of non-ablative penetration to these depths.

Figure 3A:
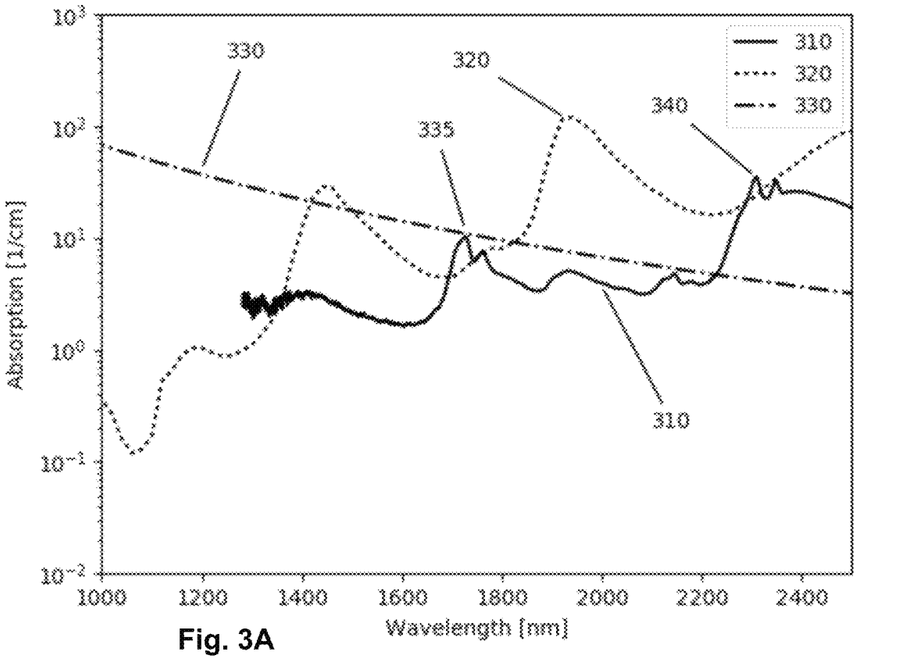
FIGS. 3A and 3B are graphs illustrating the absorption coefficients of human sebum lipid, water, and melanosomes for various wavelengths of light.
Figure 3B:
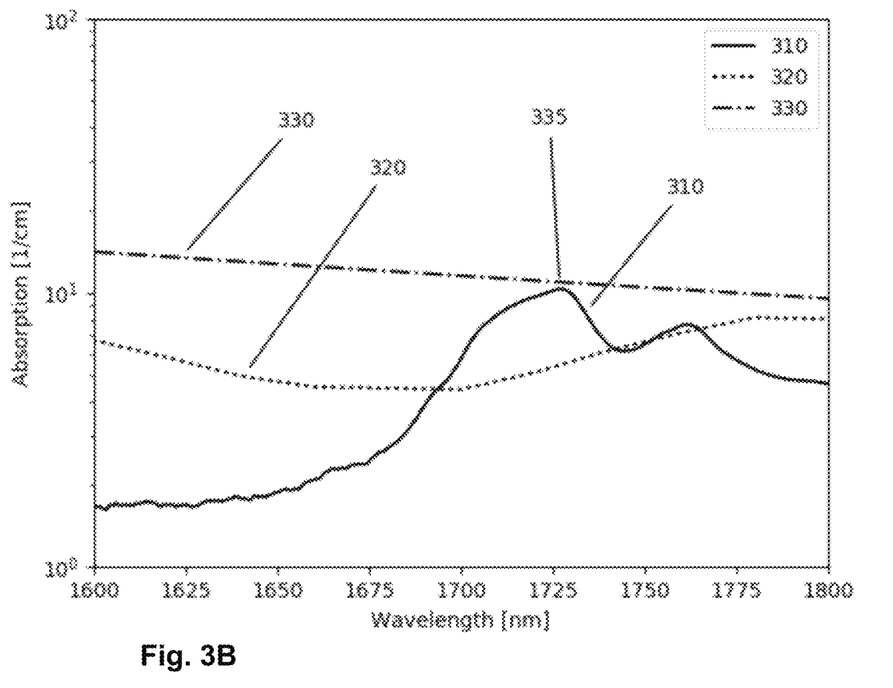

FIGS. 3A and 3B are graphs illustrating the absorption curves for several chromophores of interest (water, sebum, and melanosomes) at wavelengths of light for portions of the near-infrared spectrum (about 750 nm-1400 nm) and the short-wavelength infrared spectrum (about 1400-3000 nm). FIG. 3A illustrates the absorption curve 310 for sebum, the water absorption curve 320, and the absorption curve 330 for melanosomes. It will be appreciated that in laser treatment systems directed toward other conditions, e.g., tattoo removal or pigmented lesions, the absorption of other structures or chromophores (e.g., inks of various colors, hemoglobin, etc.) will be important considerations in selecting laser treatment system parameters such as wavelength, fluence, peak power, etc.

FIG. 3A demonstrates that the sebum absorption curve 310 has a peak at about 1727.5 nm, meaning that sebum absorbs laser light at this wavelength more strongly than light at other nearby wavelengths, e.g., 1650 nm or 1800 nm. The absorption coefficient of water is less than that of sebum in a range of from about 1693 nm to about 1742 nm, and within a range of from about 2280-2360 nm. The absorption coefficient of melanosomes exceeds that of sebum at all wavelengths less than about 2225 nm, although only by a small amount at the 1727.5 nm peak for sebum, as demonstrated at point 335 of FIG. 3A, where the two absorptions curves approach one another. It will be appreciated by persons of skill in the art that the concentration of sebum, water, and melanin may vary from patient to patient for a given area, and even within a particular patient depending upon the target tissue structure(s), the hydration status of the patient, and the skin type or area of the patient.

As shown more clearly in FIG. 3B, the absorption coefficient for sebum at a peak of about 1727.5 nm is approximately twice that of water, and is only slightly less than that of melanosomes. Specifically, the absorption coefficient for melanosomes at 1727.5 is about 11.0 cm-1, and that of sebum is about 10.3 cm-1. Accordingly, in one embodiment, the invention comprises a laser providing pulsed laser light at a wavelength of between 1693-1742 nm, more preferably at about 1720-1730 nm, and more preferably still at about 1727.5 nm.

Referring again to FIG. 3A, sebum has a further absorption peak (340) of about 2305 nm, exceeding that of both water and melanosomes at the same wavelength. Accordingly, in one embodiment, the invention comprises a laser providing pulsed laser light at a wavelength of between about 2287-2318 nm. Although sebum strongly absorbs light at 2305 nm, light at this wavelength is less suitable than light at 1727.5 nm because its penetration depth into skin is much less than that of light at 1727.5 nm. In general, at wavelengths shown in FIGS. 3A and 3B, the penetration of light decreases with increasing wavelength. Accordingly, treatment of acne and other conditions with laser light involves multiple tradeoffs, including the relative absorption coefficients of target and non-target tissues/structures, penetration depth of the wavelength of interest into skin, laser power, laser pulse fluence, pulse duration, pulse frequency, etc.

Pain associated with high-fluence laser treatments may significantly limit the application of many procedures. In particular, treatment of structures within the dermis, such as tattoo particles, sebum, or sebaceous gland tissue may result in significant pain. As discussed more fully in connection with FIG. 3A and FIG. 3B, in many such cases, the absorption coefficients of target and non-target chromophores may cause significant heat-induced pain associated with heating tissues overlying the actual target structures. Without being bound by theory, it is believed that in some instances surface oils on the stratum corneum (i.e., the outermost) layer of the epidermis may function as a heat sink to absorb laser energy that more desirably penetrates into deeper tissue structures. In one embodiment, the present invention involves methods of treating tissue by removing such oils.

Figure 4:
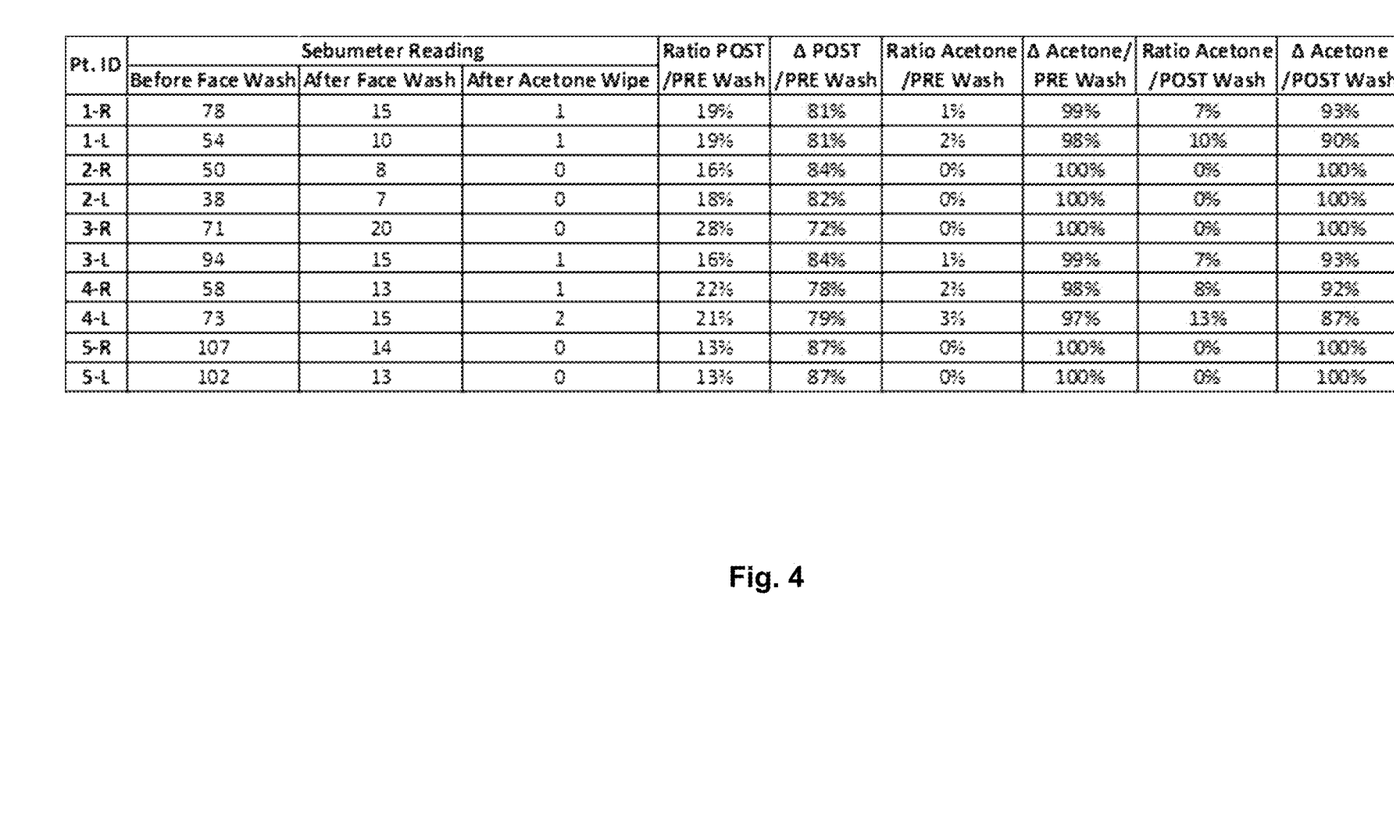
FIG. 4 is a table illustrating levels of oil reduction during treatment of skin tissue with water and an organic compound comprising acetone, respectively.

In the present disclosure oil levels were determined using a sebometer to determine relative oil levels on the surface of the skin. Initial determinations were performed prior to cleaning to establish a baseline or first oil level. An aqueous-based cleaning was performed FIG. 4 is a table illustrating various levels of oil removal using water and an organic medium. In the particular example of FIG. 4, the organic medium is acetone. In various embodiments, however, the first step may involve removal of oil using an aqueous solution other than water (e.g., buffered solutions) and other organic media may be used instead of acetone (e.g., alcohols, other ketones, other organic biocompatible solvents including mixtures). In some embodiments, the cleaning steps may involve applying water or organic media for a predetermined time period and then removing the water or organic media (e.g., using a wipe or vacuum). In some embodiments, the application and removal are accomplished together using a wipe saturated with the cleaning medium.

Figure 8:
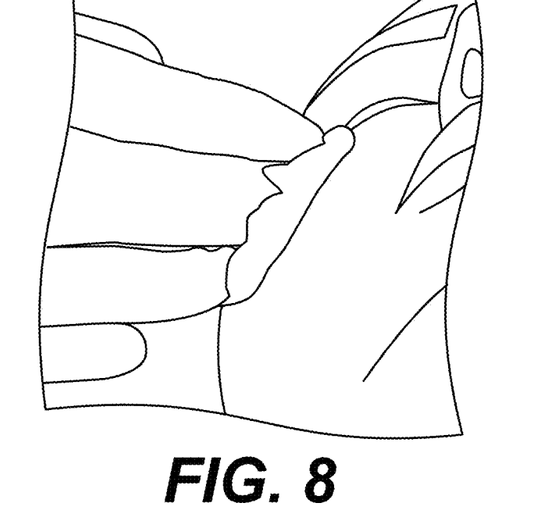
FIG. 8 is an illustration of a treatment step for removing an aqueous solution and oil from skin, according to one embodiment.

In the present disclosure oil levels were determined using a sebometer to determine relative oil levels on the surface of the skin. FIG. 4 shows oil level reduction results for 5 different patients for the left and right side of the face, respectively (column 1). An initial oil level determination was performed prior to cleaning the skin, to establish a baseline or first skin oil level, and is shown in the column 2 ("before face wash"). An aqueous-based cleaning was performed by applying water to the surface of the face and using a wipe to remove the water and oil. A second oil level was determined by remeasuring the skin in the same area following the aqueous-based cleaning step, as shown in column 3 ("after face wash"). Embodiments in which application and removal occur in a single wiping step are considered to be both within the scope of the invention. FIG. 8 illustrates in approach in which a first, aqueous agent (water) is applied to a patient's skin and is removed in a single step by a gentle wiping of the face with a water-saturated material.

Figure 9:
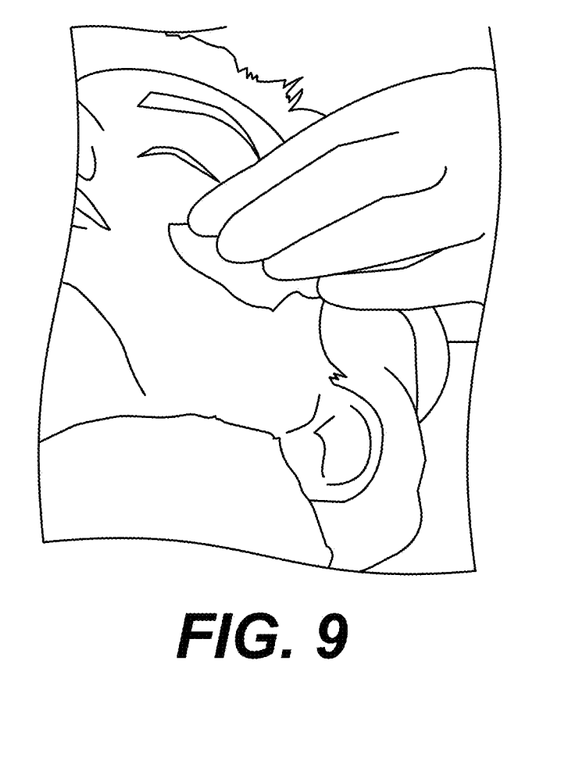
FIG. 9 is an illustration of a treatment step for removing skin oil and an agent solubilizing the skin oil, according to one embodiment.

Following the determination of the second oil level, the skin was again cleaned by applying an acetone solution and wiping the skin to again remove skin oil and acetone. FIG. 9 illustrates an approach in which a second, oil-solubilizing agent (an acetone solution) is applied to a patient's skin and removed in a single step by gently wiping the face with a material saturated with the acetone solution. In various embodiments, an acetone solution of from 0.1% to 50% acetone may be used. A third oil level was then determined by remeasuring the skin in the same area following the acetone-based cleaning step, and is shown in column 4.

Results of the cleaning steps surprisingly revealed that it is possible to lower the skin oil level, as measured by sebometer readings, by 85% or more (preferably at least 95%, and more preferably 98% or more) compared to the initial oil levels. Without being bound by theory, it is believed that in treatments in the range of 1200-1800 nm laser light, a significant pain reduction may be achieved by removing the oil that would otherwise function as a heat sink to reduce treatment efficacy.

In particular, while cleaning the skin with water was able to reduce sebometer measurements of skin oil levels, generally a significant oil level remained after aqueous cleaning alone. As shown in column 5 (ratio post/pre wash) and column 6 (Δ post/pre wash), in most cases less than a 90% reduction in oil level was achieved, and in some cases less than an 80% oil reduction resulted. More significantly, a significant amount of the oil remained on the skin compared to the initial reading, as demonstrated by the sebometer scores in column 3. By comparison, the acetone cleaning step resulting in a removal of nearly all or all of the measurable oil, with 5 of 10 scores of 0, 4 scores of 1 and only 1 score of 2. This is shown clearly in columns 7 (ratio acetone/pre wash) and 8 (Δ acetone/pre wash, which indicates that it was possible to remove in excess of 85% and more typically in excess of 95% of the oil initially present as measured by sebometer scores. In all cases, a reduction of 97% or higher from the first oil level was achieved. In some embodiments, the step of cleaning the skin with an aqueous solution may be omitted, and a single cleaning step using an agent (e.g., an organic compound) capable of at least partially solubilizing oil may be used to remove 85% or more of the oil in the skin may be performed instead.

Embodiments of the present invention, in addition to the foregoing oil removal step(s), also involve rehydrating the skin to remove any undesired air entrapped in the stratum corneum or epidermal fibers. Rehydrating the skin is preferably performed with an aqueous solution (which may also contain one or more excipients such as a buffering agent, an acid, a medicine, an antibiotic, a cleansing agent, and an optical clarifying agent). Without being bound by theory, is believed that removal of oil renders the skin dry, and the stratum corneum may resemble a mat structure of collagen or other fibrils that may entrap air. If air is entrapped in a portion of an area that receives a high-fluence laser pulse (i.e., a target skin area), uneven heating will result, with a significant risk of excessive damage to the skin and associated pain in areas that are not overlaid by entrapped air. Accordingly, embodiments of the present disclosure further involve removal of small air pockets in the stratum corneum of the epidermis by using a rehydrating medium.

Finally, embodiments herein involve providing contact cooling to cool a first skin area that includes one or more target skin areas that receive laser pulses. Even with the foregoing cleaning and rehydration steps, high-fluence laser energy and result in burns to overlying skin tissue (e.g., epidermal tissues overlying a dermal target structure). This is particularly likely where the fluence exceeds 15 J/cm2. Accordingly, in embodiments disclosed here, the skin is directly cooled by contact cooling to lower the temperature of the epidermis and other overlying structures to minimize the risk of pain. Many structures relating to pain signals are located at or near the dermal/epidermal junction, and by provide cooling the overlying tissue in combination with the foregoing oil removal and rehydration steps, it is possible to achieve treatment methods that allow a deeper target structure (e.g., in the dermis) to be heated to a desired treatment temperature while ensuring that pain-associated structures overlying the target remain below a temperature likely to cause significant pain.

Prior art approaches to deep-tissue treatment have frequently used non-contact cooling such as blown air. Without being bound by theory, contact cooling is believed to provide a higher thermal coupling coefficient that, combined with the foregoing steps, can provide more advantageous cooling for high-fluence laser. It is noted that where low-fluence lasers are used, the risk of skin damage is not as acute as in high-fluence lasers as recited herein. Accordingly, it is believed that the foregoing steps, in combination, can be used to provide improved treatments for deep-tissue (e.g., dermal) structures with high-fluence lasers.

In one embodiment, the present invention involves methods of reducing pain perceived by a patient in response to a treatment of a target skin area with high-fluence therapeutic laser light by treating the skin with dimethyl sulfoxide (DMSO) prior to treatment with the high-fluence laser. Without being bound by theory, it is believed that DMSO may function by one or more mechanisms to facilitate pain reduction, including by improving the optical clarity of the skin thereby enabling more of the laser energy to penetrate into deeper structures without scattering in overlying tissues, or by binding to one or more neural structures to impede pain signals.

Figure 5:
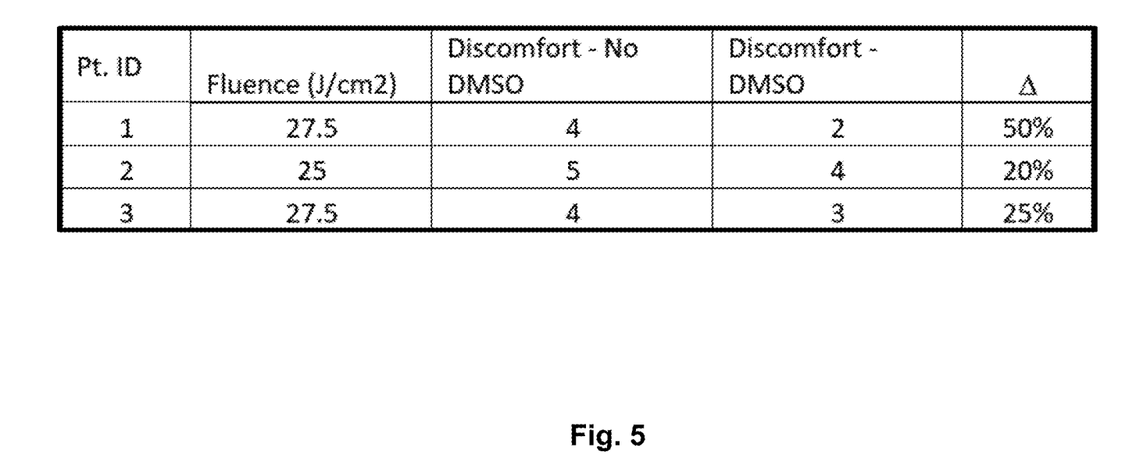
FIG. 5 is a table illustrating a level of perceived discomfort reduction in patients treated with and without a solution comprising dimethyl sulfoxide (DMSO)

FIG. 5 illustrates an example of pain reduction achieved in treating three patients with DMSO. Each patient was treated with high-fluence laser light on one side of the face without pretreatment with DMSO, and on the other side with the same high-fluence light but following pretreatment with DMSO. As shown in column 2, relatively high fluences of 27.5 J/cm2 (patients 1 and 3) and 25 J/cm2 were used. A scale of 1-10 to measure pain was used, and each patient perceived a level of pain as a 4 or 5 with no DOMS. Treatment of the other side of the face following treatment with DMSO resulting in pain levels of 2-4, and a pain reduction ranging from 20-50%. Accordingly, in certain embodiments, the present disclosure comprises a method of reducing pain levels by applying DMSO to a skin area to be treated, waiting for a predetermined time period of 1-50 minutes, and more preferably from 5-50 minutes, following to applying the high-fluence therapeutic laser light to the skin area to be treated.

Figure 6:
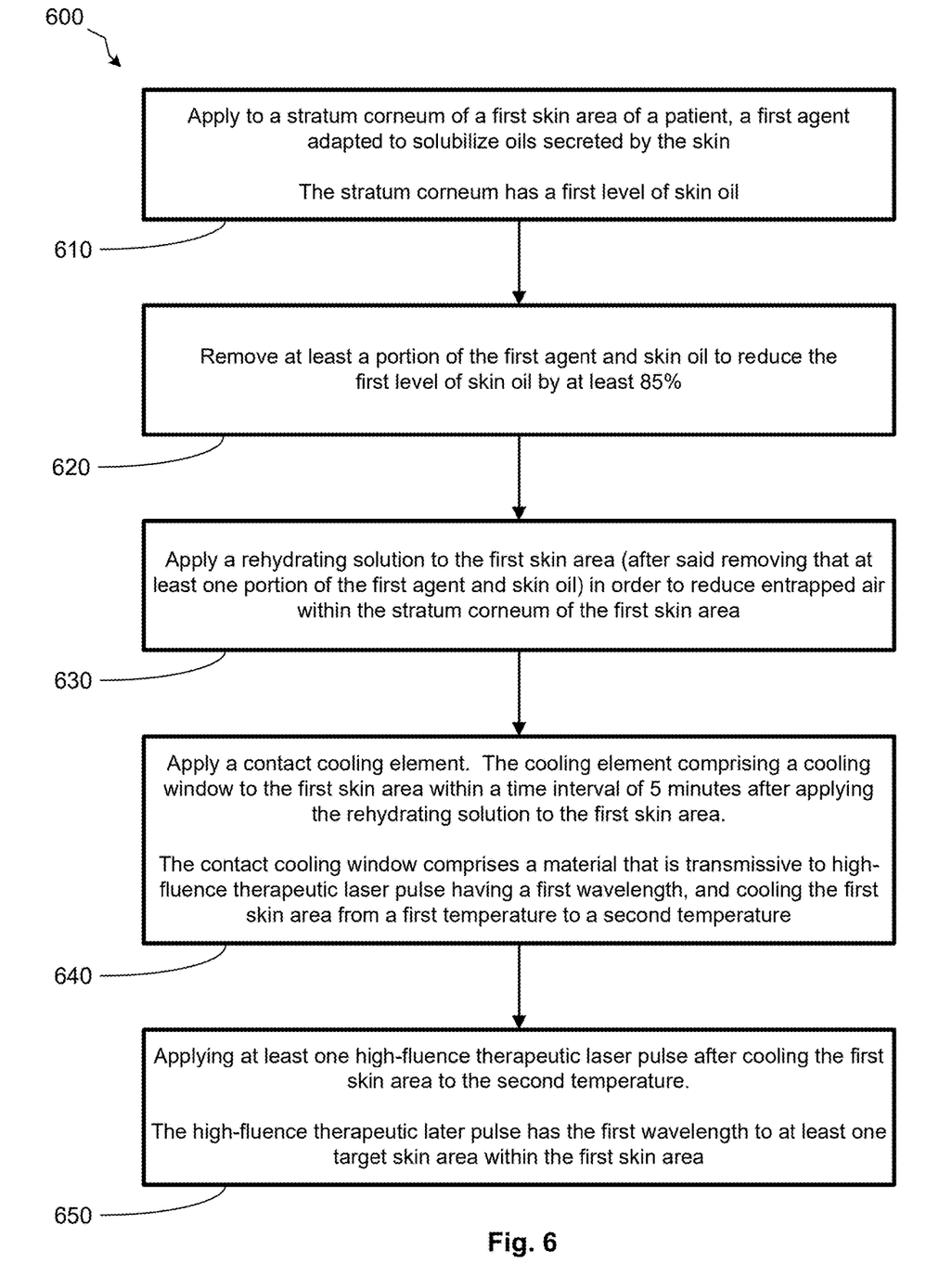
FIG. 6 is a flowchart of a method according to an embodiment of the present disclosure.

FIG. 6 illustrates a method 600 of reducing a level of pain associated with treating a target skin area with high-fluence laser light, in which the target skin area comprises an epidermis layer and a dermis layer. The method comprises applying a first agent to a stratum corneum of a first skin area of the patient (610), in which the first agent is adapted to solubilize oils secreted by the skin, and in which the stratum corneum has a first level of skin oil associated with it. The method further comprises removing at least a portion of the first agent and skin oil to reduce the first level of skin oil by at least 85% (620). After the first agent and skin oil removal step, the method comprises applying a rehydrating solution to the first skin area (630), which reduces entrapped air within the stratum corneum of the first skin area. The method further comprises applying a contact cooling element that comprises a cooling window to the first skin area to cool the first skin area from a first temperature to a second (lower) temperature (640). The contact cooling element is applied to the first skin area within a time interval of 5 minutes after the step of applying the rehydrating solution (i.e., within 5 minutes after step 630 is completed). Finally, the method comprises, after step 640, applying at least one high-fluence laser pulse having a first wavelength to at least one target skin area within the first skin area (650). In some embodiments, this may comprise applying a plurality of high-fluence laser pulses to different, smaller target skin areas within the first skin area being cooled.

Figure 7:
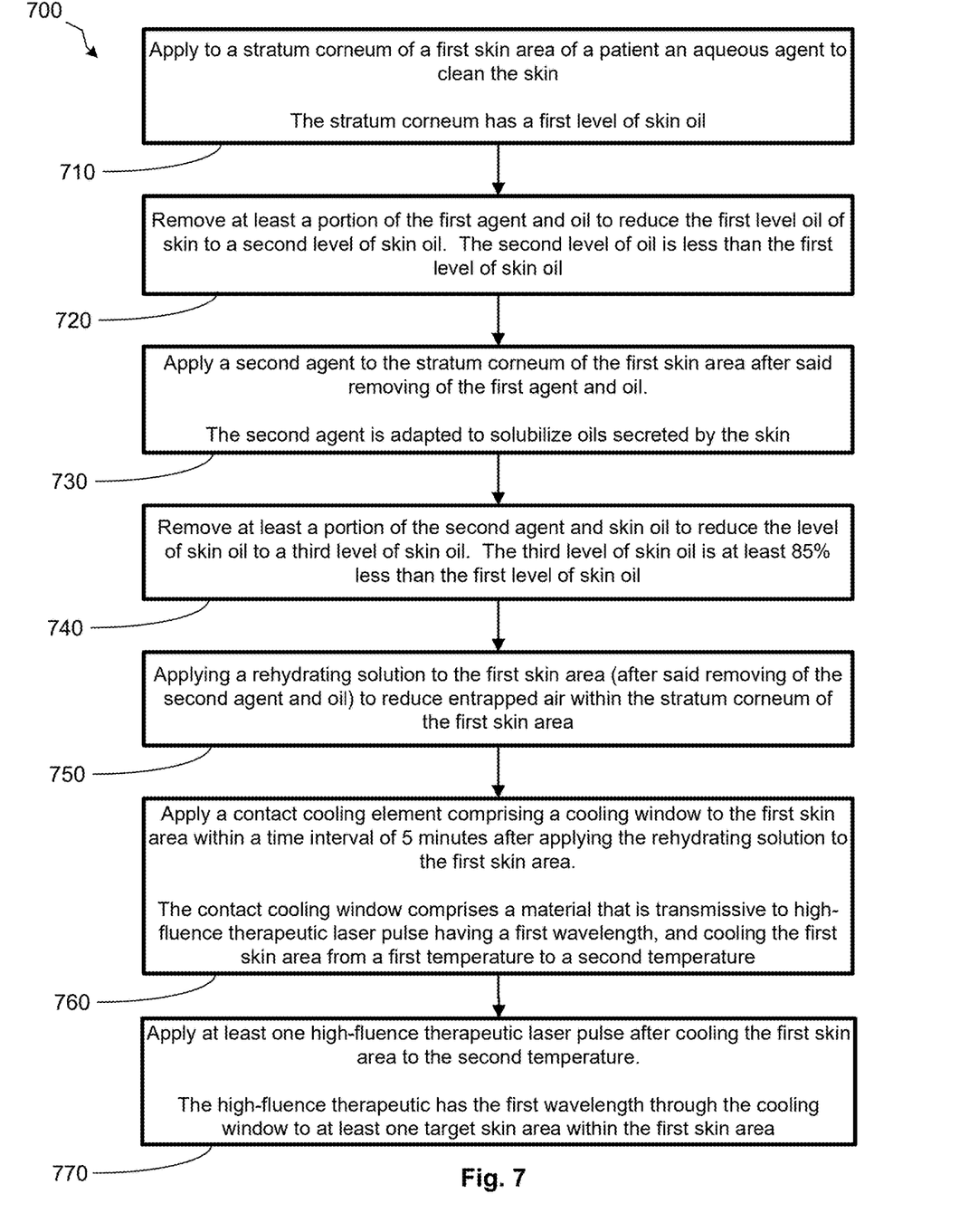
FIG. 7 is a flowchart of a method according to another embodiment of the present disclosure.

FIG. 7 illustrates a method 700 of treating the skin of a patient to reduce a level of pain associated with treating a target skin area with high-fluence laser light, in which the target skin area comprises an epidermis layer and a dermis layer. The method comprises applying a first, aqueous agent to a stratum corneum of a first skin area of a patient (710), in which the aqueous agent is applied to clean the skin and the stratum corneum has a first level of skin oil associated with it. After the application step, the method comprises removing at least a portion of the first, aqueous agent and skin oil (720) to reduce the first level of skin oil to a second level of skin oil that is less than the first level of skin oil. The method further comprises, after removing the first, aqueous agent and oil, applying a second agent to the stratum corneum of the first skin area of the patient (730), in which the second agent is adapted to solubilize oils secreted by the skin. The method further comprises removing at least a portion of the second agent and skin oil to reduce the level of skin oil to a third level of skin oil that is at least 85% less than the first level of skin oil (740). After the second agent and skin oil removal step, the method comprises applying a rehydrating solution to the first skin area (750), which reduces entrapped air within the stratum corneum of the first skin area. The method further comprises applying a contact cooling element that comprises a cooling window to the first skin area to cool the first skin area from a first temperature to a second (lower) temperature (760). The contact cooling element is applied to the first skin area within a time interval of 5 minutes after the step of applying the rehydrating solution (i.e., within 5 minutes after step 750 is completed). Finally, the method comprises, after step 760, applying at least one high-fluence laser pulse having a first wavelength to at least one target skin area within the first skin area (770). The pulses are applied through the cooling window. In some embodiments, this may comprise applying a plurality of high-fluence laser pulses to different, smaller target skin areas within the first skin area being cooled.

Reference throughout this specification to "one example," "an example," "embodiment," and/or "another example" should be considered to mean that the particular features, structures, or characteristics may be combined in one or more examples. Any combination of any element in this disclosure with any other element in this disclosure is hereby disclosed. For example, an element on a first page can be combined with any element in this document (e.g., an element from a second page).

While there has been illustrated and described what are presently considered to be example features, it will be understood by those skilled in the art that various other modifications may be made, and equivalents may be substituted, without departing from the disclosed subject matter. Additionally, many modifications may be made to adapt a particular situation to the teachings of the disclosed subject matter without departing from the central concept described herein. Therefore, it is intended that the disclosed subject matter not be limited to the particular examples disclosed.

What is claimed is:

1. A method of reducing a level of pain perceived by a patient in response to a pain-inducing treatment of a target skin area with high-fluence therapeutic laser light, the target skin area comprising an epidermis layer and a target structure within a dermis layer, the method comprising:
    a) applying to a stratum corneum of a first skin area of the patient a first agent adapted to solubilize oils secreted by the skin, the stratum corneum having a first level of skin oil associated therewith;
    b) removing at least a portion of the first agent and the skin oil to reduce the first level of skin oil by at least 85%;
    c) after said removing, applying an aqueous rehydrating solution to the first skin area to reduce entrapped air within the stratum corneum of the first skin area without applying oil to the stratum corneum;
    d) applying a contact cooling element comprising a cooling window to the first skin area within a time interval of 5 minutes after applying the rehydrating solution to the first skin area, wherein the contact cooling window comprises a material that is transmissive to the high-fluence therapeutic laser light having a first wavelength at which the absorption coefficient of sebum exceeds the absorption coefficient of water, and cooling the first skin area from a first temperature to a second temperature, the first wavelength ranging from 1200 nm to 1800 nm; and
    e) after cooling the first skin area to the second temperature, applying at least one high-fluence therapeutic laser light pulse having the first wavelength through the cooling window to the target skin area within the first skin area, wherein steps (a)-(c) are adapted to reduce the absorption of therapeutic laser light pulse energy in the epidermis layer and increase the amount of therapeutic laser pulse energy reaching the target structure.

2. The method of claim 1, wherein the first agent comprises one or more of an acetone solution and an alcohol solution.

3. The method of claim 1, wherein said removing step comprises removing the skin oil sufficient to reduce the first level of skin oil by at least 90%.

4. The method of claim 1, wherein said removing step comprises removing the oil sufficient to reduce the first level of skin oil by at least 95%.

5. The method of claim 1, wherein the first skin area is an area to be treated for acne, and wherein applying the at least one high-fluence therapeutic laser pulse having the first wavelength comprises applying a therapeutic laser pulse having a fluence of at least 15 J/cm$^2$.

6. The method of claim 1, applying the rehydrating solution comprises applying the rehydrating solution selected from water and an aqueous solution comprising one or more of a buffering agent, an acid, a medicine, an antibiotic, a cleansing agent, and an optical clarifying agent.

7. The method of claim 1, further comprising: f) applying an optical clarifying agent to the target skin area within the first skin area; and g) waiting for a first time interval ranging from 1 minute to 60 minutes after applying the optical clarifying agent, to reduce optical scattering in the target skin area of the first skin area; wherein applying the at least one high-fluence therapeutic laser pulse to the target skin area occurs after the first time interval has elapsed.

8. The method of claim 7, wherein the optical clarifying agent comprises dimethyl sulfoxide (DMSO).

9. The method of claim 1, wherein applying the at least one high-fluence therapeutic laser pulse comprises applying one or more laser pulses having a fluence in the range of 5-40 J/cm2.

10. The method of claim 1, wherein applying the at least one high-fluence therapeutic laser pulse comprises applying one or more laser pulses having a fluence in the range of 10-25 J/cm2.

11. The method of claim 1, wherein applying the contact cooling element comprising the cooling window to the first skin area comprises applying the contact cooling window to the first skin area within a time interval of 2 minutes after applying the rehydrating solution.

12. The method of claim 1, wherein applying the contact cooling element comprising the cooling window to the first skin area comprises applying the contact cooling window to the first skin area within a time interval of 1 minute after applying the rehydrating solution.

13. The method of claim 1, wherein the step of applying the first agent comprises: 1) determining the first level of skin oil; and 2) applying the first agent to the stratum corneum after determining the first level of skin oil.

14. The method of claim 1, wherein the step removing at least the portion of the first agent and the oil comprises: 1) removing at least the portion of the first agent and the skin oil; and 2) after the removing, determining a second level of skin oil.

15. The method of claim 14, wherein the step of removing at least the portion of the first agent and the oil comprises: 3) repeating the steps of removing at least the portion of the first agent and the oil and determining the second level of skin oil until the first level of skin oil has been reduced by at least 85%.

16. The method of claim 1, wherein the first agent comprises at least one organic agent capable of at least partially solubilizing the skin oil.

17. A method of treating the skin of a patient to reduce a level of pain associated with treating a target skin area with high-fluence therapeutic laser light, the target skin area comprising an epidermis layer and a target structure within a dermis layer, the method comprising:
    a) applying to an epidermis of a first skin area of the patient an oil-removing agent, the epidermis of the first skin area having a first level of skin oil associated therewith;
    b) removing at least a portion of the oil-removing agent and the skin oil sufficient to reduce the first level of skin oil in the epidermis of the first skin area by at least 85%;
    c) after said removing, applying an aqueous rehydrating solution to the epidermis of the first skin area to reduce entrapped air within the epidermis of the first skin area without applying oil to the stratum corneum;
    d) applying a contact cooling element comprising a cooling window to the first skin area within a time interval of 5 minutes after applying the rehydrating solution to the epidermis of the first skin area, wherein the contact cooling window comprises a material that is transmissive to the high-fluence therapeutic laser light having a first wavelength at which the absorption coefficient of sebum exceeds the absorption coefficient of water, and cooling the first skin area from a first temperature to a second temperature, the first wavelength ranging from 1200 nm to 1800 nm; and e) after cooling the first skin area to the second temperature, applying at least one high-fluence therapeutic laser light pulse having the first wavelength through the cooling window to the target skin area within the first skin area, wherein steps (a)-(c) are adapted to reduce the absorption of therapeutic laser light pulse energy in the epidermis and increase the amount of therapeutic laser pulse energy reaching the target structure.

18. The method of claim 17, wherein applying at least one high-fluence therapeutic laser pulse comprises applying one or more laser pulses having a fluence in the range of 8-28 J/cm2.

19. A method of treating the skin of a patient to reduce a level of pain associated with treating a target skin area with high-fluence therapeutic laser light, the target skin area comprising an epidermis layer and a dermis layer, the method comprising:
   a) applying to a stratum corneum of a first skin area of the patient a first, aqueous agent to clean the skin, the stratum corneum having a first level of skin oil associated therewith;
   b) removing at least a portion of the first agent and the oil to reduce the first level of skin oil to a second level of skin oil that is less than the first level of skin oil;
   c) after said removing of the first, aqueous agent and oil, applying to the stratum corneum of the first skin area a second agent adapted to solubilize oils secreted by the skin;
   d) removing at least a portion of the second agent and the skin oil to reduce the second level of skin oil to a third level of skin oil that is at least 85% less than the first level of skin oil;
   e) after said removing of the second agent and the oil, applying an aqueous rehydrating solution to the first skin area to reduce entrapped air within the stratum corneum of the first skin area without applying oil to the stratum corneum;
   f) applying a contact cooling element comprising a cooling window to the first skin area within a time interval of 5 minutes after applying the rehydrating solution to the first skin area, wherein the contact cooling window comprises a material that is transmissive to the high-fluence therapeutic laser light having a first wavelength at which the absorption coefficient of sebum exceeds the absorption coefficient of water, and cooling the first skin area from a first temperature to a second temperature the first wavelength ranging from 1200 nm to 1800 nm; and
   g) after cooling the first skin area to the second temperature, applying at least one high-fluence therapeutic laser light pulse having the first wavelength through the cooling window to the target skin area within the first skin area, wherein steps (a)-(e) are adapted to reduce the absorption of therapeutic laser light pulse energy in the epidermis and increase the amount of therapeutic laser pulse energy reaching the target structure.

20. The method of claim 19, wherein the level of pain perceived by the patient is less than a level of pain associated with not following the method of claim 19.

* * * * *